United States Patent [19]
Hollis et al.

[11] Patent Number: 4,789,489
[45] Date of Patent: Dec. 6, 1988

[54] METHOD FOR THE CONTROL OF MOLLUSKS

[75] Inventors: C. George Hollis, Germantown; Richard W. Lutey, Memphis, both of Tenn.

[73] Assignee: Buckman Laboratories International, Inc., Memphis, Tenn.

[21] Appl. No.: 160,997

[22] Filed: Feb. 26, 1988

[51] Int. Cl.$^4$ ................................. C02F 1/50
[52] U.S. Cl. ..................... 210/755; 210/764; 210/765; 71/67; 514/642
[58] Field of Search ............ 210/755, 764–766; 71/67; 514/642

[56] References Cited

U.S. PATENT DOCUMENTS

| | | | |
|---|---|---|---|
| 3,771,989 | 11/1973 | Pera et al. | 71/67 |
| 3,898,188 | 8/1975 | Rembaum et al. | 514/642 X |
| 4,018,592 | 4/1977 | Buckman et al. | 71/67 |
| 4,054,542 | 10/1977 | Buckman et al. | 260/2 BP |
| 4,140,798 | 2/1979 | Merianos et al. | 424/325 |
| 4,174,406 | 11/1979 | Bordenca | 514/642 X |
| 4,462,914 | 7/1986 | Smith | 210/755 |
| 4,561,983 | 12/1985 | Davis et al. | 210/755 |
| 4,579,665 | 4/1986 | Davis et al. | 210/755 |
| 4,581,058 | 4/1986 | Fenyes et al. | 71/67 |
| 4,643,835 | 2/1987 | Koeplin-Gall et al. | 210/764 X |

OTHER PUBLICATIONS

Rembaum, Biological Activity of Ionene Polymers, 22 Applied Polymer Symposium 299–317 (1973).

*Primary Examiner*—Tom Wyse
*Attorney, Agent, or Firm*—Finnegan, Henderson, Farabow, Garrett & Dunner

[57] ABSTRACT

A method for the control of fouling by marine and fresh water mollusks through the use of an ionene polymer. The disclosed method is particularly useful in controlling fouling by species of fresh water Asiatic clams of the genus Corbicula, the most common of which is *C. fluminea*.

22 Claims, No Drawings

METHOD FOR THE CONTROL OF MOLLUSKS

FIELD OF THE INVENTION

This invention is concerned with a method for the control of fouling by marine and fresh water mollusks through the use of ionene polymers.

Particularly, this invention relates to the control of mollusks which foul underground irrigation systems; municipal water treatment facilities; river sand and gravel operations; and industrial facilities utilizing raw water, particularly for cooling and fire protection systems. More particularly, this invention relates to the control of fouling by fresh water mollusks in fresh water systems, especially by species of Asiatic clams of the genus Corbicula, the most common of which is *Corbicula fluminea* (hereafter, "*C. fluminea*").

BACKGROUND OF THE INVENTION

U.S. Pat. No. 4,462,914 discloses a method of controlling Corbicula in aqueous systems comprising treating said systems with a cationic polymer. This patent, however, does not teach the use of ionene polymers as in the instant invention. For example, the preferred compound [DMDAAX$^\ominus$] of this reference has the structure:

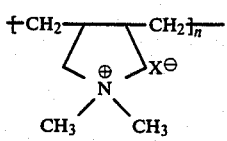

and does not, as such, contain nitrogen cations in the backbone of the polymer as do the ionene polymers of the instant invention. Ionene polymers have been employed in the control of simple microorganisms—such as bacteria and algae—but these organisms, unlike mollusks, are not complex macroinvertebrates.

Problems of fouling are caused by the attachment and growth of juvenile mollusks in service and cooling water systems, and the settlement of young adults in condenser tubes of condenser water systems, causing deleterious effects to the operation and safety of these systems. In fossil-fueled systems, problems have been related to plugging of condenser tubes, surface water heat exchangers, and fire protection systems. In nuclear power plants, additional problems of blockage may occur, including the shutdown of service water and emergency reactor cooling systems.

Among the most serious threats posed by *C. fluminea* is its macrofouling of nuclear and fossil-fueled power generating stations. In power plants, the shells of living and dead clams foul steam condensers and service water systems. Clams enter these systems as juveniles or adults carried on water currents and settle, grow, reproduce and accumulate in numbers that reduce water flow to levels that seriously compromise or prevent operation. (Goss et al., *Control studies for Corbicula on steam electric generating plants*, J. C. Britton (Ed.), Proceedings, First International Corbicula Symposium, Texas Christian University Research Foundation, Fort Worth, Tex., pp. 139–151 (1979)).

*C. fluminea* is a particularly dangerous macrofouling species in nuclear power plants because it simultaneously fouls primary and secondary (backup) systems, thus compromising fail-safe operation (Henegar et al., *Bivalve Fouling of Nuclear Plant Service-Water Systems. Factors that may Intensify the Safety Consequences of Biofouling*, NRC FIN B2463, NUREG/CR-4070, PNL-5300, Vol. 3 Div. Radiation Programs and Earth Sciences, Office of Nuclear Regulatory Research, U.S. Nuclear Regulatory Commission, Washington, D.C., 51 pp. (1985)). Major biofouling incidents have been reported at nuclear power stations in Arkansas (Arkansas Nuclear I), Brown's Ferry, Ala., and Baldwin, Ill. (Henegar et al., above). Such incidents have led to the issuance of a bulletin by the U.S. Nuclear Regulatory Agency (U.S. Nuclear Regulatory Agency (USNRC), *Flow Blockage of Cooling Water to Safety Components*, Bulletin No. 81-03, Office of Inspection and Enforcement, United States Nuclear Regulatory Commission, Washington, D.C. 6 pp. (1981)) requiring all nuclear power stations in the U.S. to inspect for and report the presence of this species in their operations and raw water sources. Analysis of this and other data has indicated that of the 32 nuclear power stations within the known geographic range of *C. fluminea* in the U.S., 19 already report infestations of varying severity and 11 others are in close proximity to known populations (Counts, *Distribution of Corbicula fluminea at Nuclear Facilities*, NRC FIN B8675, NUREG/CR-4233, Div. Engineering, Office of Nuclear Reactor Regulation, U.S. Nuclear Regulatory Commission, Washington, D.C. 79 pp. (1985)). Thus, macrofouling by *C. fluminea* presently poses a dangerous and costly problem in the nuclear industry.

Within the known geographic range of *C. fluminea* in the United States lie hundreds of fossil-fueled electric power stations whose raw water systems are also subject to macrofouling by this species. As in nuclear plants, such macrofouling requires expensive shutdowns for repair and replacement of damaged equipment, as well as expensive and often futile retrofitting of anti-fouling equipment that has generally proved ineffective in controlling clam impingement.

While a number of control methodologies have been developed to reduce the macrofouling of industrial and power station service water systems by *C. fluminea*, none has proved completely effective.

Control of *C. fluminea* macrofouling in power station and industrial service and auxilliary water systems has primarily been through chlorination. Recommended residuals of chlorine are 0.5–1.0$\mu$g per liter for continuous application or 500 $\mu$g per liter for periods of 100–500 hrs. to kill juvenile clams borne on intake currents into these systems (Cherry et al., *Corbicul fouling and control measures at the Celco Plant, Virginia*, Am. Malacol. Bull. Special Ed. No. 2, pp. 69–81 (1986); Mattice, *Freshwater macrofouling and control with emphasis on Corbicula*, Symposium on Condenser Macrofouling Control Technologies: The State of the Art, Electric Power Research Institute, Palo Alto, Calif., pp. 4-1–4-30 (1983); and Sinclair et al., *Further Studies on the Introduced Asiatic Clam (Corbicula) in Tennessee*, Tennessee Stream Pollution Control Board, Tennessee Department of Public Health, Nashville, 76 pp. (1963)).

As chlorination is generally only allowed by U.S. Environmental Protection Agency regulations for 2 of every 24 hrs. in systems returning service water to source (U.S. Environmental Protection Agency (USEPA), *Effluent limitations guidelines, pretreatment standards and new source performance standards under Clean Water Act; steam electric power generating point source catecory*, 40 CFR, Parts 125 and 423, Fed. Regist. 45(200):68328–68337 (1980)), it has proved to be generally ineffective in controlling *C. fluminea* macrofouling (Page et al., *Biofouling of power plant service water systems by Corbicula*, Am. Malacol. Bull. Special Edition No. 2: 41-45 (1986)). Heavier chlorination may also exacerbate corrosion of pipes, and when *C. fluminea* burrows into accumulations of corrosion products and silt in the low flow areas of these systems it effectively becomes insulated from the toxic effects of chlorination (Johnson et al., *Engineering factors influencing Corbicula fouling in nuclear service water systems*, Am. Malacol. Bull. Special Ed. No. 2: 47-52 (1986)).

Mattice, above, reports a number of molluscicides other than chlorine that have been tested for efficacy in control of *C. fluminea*, but have proved ineffective or impractical. Antifouling paints, coverings and slow release toxic pellets appear effective in killing clams (Mattice, above), but their relatively short half-lives, and difficulties in application, make their utilization in existing service water systems neither feasible nor cost effective.

Therefore, there is a major incentive for the development of an environmentally safe, cost effective, highly potent molluscicide to control macrofouling by *C. fluminea* in industrial and power generation raw water systems. To date no molluscicide of those described above has proved to be completely satisfactory for the control of *C. fluminea* macrofouling in the raw water systems of power stations or other industrial operations.

The biology of bivalve mollusks, including such species as *C. fluminea* (Asiatic clam), is especially suited for their establishment and growth in the water systems of power plants. The Asiatic clam occurs in great abundance in fresh water systems. McMahon and Williams (McMahon et al., *A reassessment of growth rate, life span, life cycles and population dynamics in a natural population and field caged individuals of Corbicula fluminea (Muller) (Bivalvia: Corbiculacea)*, Am. Malacol. Bull. Special Ed. No. 2, pp. 151-166 (1986)) measured a population of 1000 clams per square meter in the Trinity River and Benbrook Lake area in Texas. Since power generating stations require a large quantity of service water, they are located on major streams or lakes. The water is drawn from the supply source through a canal. Clams find these canals to be favorable for the production of their larval offspring which may be many thousands per clam. The larval stages and small adults are small enough to pass through the screens used to retard the passage of detritus into the plant. The larvae will then attach themselves to surfaces by their suctorial foot and the elaboration of mucilaginous byssal attachment threads.

Once attached, the juveniles mature into adults. In one to three months, the juveniles and small adults can grow in size so that when carried by currents into the condenser tubes, they can lodge in the tubes and cause the accumulation of small particles of material behind them, thereby completely plugging the tube. If enough tubes become plugged in this manner, the flow of water through the condenser is reduced to levels which seriously affect its efficiency, thereby forcing unit shutdown and manual removal of accumulated shells and other debris.

Clams do not grow in the condenser tubes, but are carried there by the currents from the water supply, particularly the embayment following screening. Juvenile clams carried into service water systems will mature in situ. and such systems will be plugged both by the adults produced in place and by those which are brought in by currents. Therefore, the control of fouling may be accomplished by killing the adult clams, the juvenile clams, or by preventing the attachment of the juveniles to surfaces.

DESCRIPTION OF THE INVENTION

The ionene polymers of the instant invention may be defined as polyelectrolytes with positively charged nitrogen atoms located in the backbone of polymeric chains. Examples of methods of preparation of such polymers include the polycondensation of diamines (for example, $\alpha,\omega$-ditertiary amines) with dihalides (for example, $\alpha,\omega$-dihalocompounds), the polycondensation of halo amines, or by reacting secondary amines such as dimethylamine with epichlorohydrin. Such methods produce polyammonium salts with positive nitrogens in the backbone. (See, for example, Rembaum, *Biological Activity of Ionene Polymers*, 22 Applied Polymer Symposium 299-317 (1973)).

Exemplary ionene polymers which may be employed in the process of the instant invention include those ionene polymers disclosed in U.S. Pat. Nos. 3,771,989, 4,018,592, 4,054,542, 4,581,058 and 4,140,798, all incorporated herein by reference.

Both straight- and branched-chain ionene polymers have been found to be molluscicidal to adult mollusks. In addition, it has been found that straight-chain ionene polymers are especially useful in killing juvenile mollusks, and in preventing their attachment to surfaces. Branched-chain ionene polymers may also be employed in the control of juveniles, but may require higher treatment levels than straight-chain ionene polymers.

Some crosslinking may be present in the ionene polymers employed in the instant invention. However, non-crosslinked polymers are preferred, since crosslinking may tend to reduce the effectiveness of ionene polymers in the control of mollusks.

The effective amount of ionene polymer needed to control fouling by mollusks may readily be determined by one skilled in the art. Amounts ranging from 0.5 to 500 parts of the polymer to one million parts of water are preferred.

A preferred embodiment of the invention comprises the addition of a straight-chain ionene polymer to the incoming canal or embayment water in an amount effective to kill the larval forms before they settle and mature into adult mollusks. Such addition thereby provides inhibition of mollusk infestation with its subsequent blockage of the structural parts of internal water systems. An added feature is the reduction in the number of larvae which become attached to the internal surfaces of the water system, avoiding their consequent growth into adults. By extension of the treatment rate, the destruction of adult mollusks is accomplished, eradicating problems of fouling by the adults.

The addition of a branched-chain ionene polymer in an effective amount to the incoming water will kill adult mollusks. Preferably, the amount will range from 0.5 parts to 500 parts of the polymer to one million parts of water.

Ionene polymers are suited for treatment of aqueous systems, such as those found in power generating facilities, because they ma be used in low concentrations and are dissipated in the treatment process by adsorption to suspended matter. It is therefore unlikely that use of the polymers in water systems will cause contamination of the receiving body of water.

The following examples illustrate certain embodiments of the invention and should not be regarded as limiting the scope and spirit of the invention.

EXAMPLE 1

Discussion

The efficacy of a straight-chain ionene polymer was documented in laboratory experiments using juvenile and adult forms of the Asiatic clam, *C. fluminea*. Poly[oxyethylene(dimethyliminio)ethylene(dimethyliminio)ethylene dichloride] was prepared by the method disclosed in U.S. Pat. No. 3,771,989 and tested as a 60% solution in water, hereinafter referred to as BULAB® 6002 polymer.

Juveniles: Materials and Methods

For static tests of toxicity of BULAB® 6002 polymer to juvenile *C. fluminea*, gravid adults were collected from the Clear Fork of the Trinity River near Arlington, Tex., and returned immediately to the laboratory. On return, selected adults were placed in one liter of dechlorinated tap water in glass culture dishes and held overnight in an incubator adjusted to field water temperature. The following morning, adults were removed from the culture dishes, and all spawned, viable juvenile clams (shell length approximately 2 mm) were collected individually and transferred to glass petri dishes containing 20 mL of dechlorinated city of Arlington tap water. Twenty-five juveniles were placed in each of three replicate dishes for each concentration of the product tested. Three control dishes containing twenty-five juveniles, and no molluscicide, were also set up. For test purposes, BULAB® 6002 polymer was diluted with dechlorinated tap water so that when 20 mL of the dilution were added to the petri dishes containing the juveniles, final concentrations of 2, 4 and 8 ppm of BULAB® 6002 polymer were achieved in the 40 mL of fluid. The control dishes received another 20 mL aliquot of Lake Arlington tap water. All the dishes were adjusted to pH 7 when necessary. The dishes were covered and held at 24° C. in a constant temperature room. Observations were made on the viability of the juveniles every two hours during the first 24 hours, at 6 hour intervals during the next 48 hours, and every 12 hours thereafter until either 100% mortality had been achieved, or for 7 days. Viability was determined under a 30× microscope by observation of heartbeat, gill ciliary activity, and by the maintenance of high levels of foot activity. Juveniles not displaying these characteristics, and which were unresponsive to touch by a fine camel hair brush, were removed from the dishes and counted as dead. Mortality figures were recorded at intervals based on seventy-five exposed juveniles.

Adults: Materials and Methods

Adult clams were collected from the Clear Fork of the Trinity River in Texas and transported immediately to the laboratory. The adults were habituated to dechlorinated city of Arlington, Tex. tap water for 2 days before experimentation. For each concentration of BULAB® 6002 polymer tested, and for the controls with no BULAB® 6002 polymer, three sets of twenty-five adults each were placed in 18 liters of solution in plastic holding tanks and held at 24° C. The experimental adults were selected to provide the size range of *C. fluminea* found in their natural habitat (5-35 mm in shell length). The tanks were maintained under constant aeration for the duration of the experiment, and the solutions were changed every 4 days. Periodically, all clams were checked for viability by noting the resistance to the entry of a blunted needle between the valves and, if needed, by examination of heartbeat after forcing the valves open. In the cases where adults closed their valves tightly when exposed to the several concentrations of the test chemicals, provision was made to artificially keep their valves open by inserting a plastic tab between the valves to insure continuous contact of the mollusk body with the products. Such organisms were termed "gaping adults". A total of seventy-five adults were exposed to each of the concentrations of BULAB® 6002 polymer, and to the untreated control tanks.

Experimental Results

The following is a summary of the results obtained from toxicity tests of BULAB® 6002 polymer to the Asiatic clam, *C. fluminea*.

| Group | Treatment level (ppm) | Mean Time to Death (hr) | LT50 | LT100 | Mean Percent Not Attached |
|---|---|---|---|---|---|
| Juveniles | 2 | 129.0 | 85.5 | 275 | 86.3 |
|  | 4 | 87.9 | 48.6 | 204 | 92.5 |
|  | 8 | 74.4 | 45.6 | 168 | 88.0 |
| Control (48.1% dead after 96 hour exposure) | | | | | |
| Normal Adults | 2 | 64.0 | 54.3 | 113 | — |
|  | 4 | 58.2 | 49.5 | 101 | — |
|  | 8 | 59.5 | 44.8 | 101 | — |
| Control (0% dead after 113 hour exposure) | | | | | |
| Gaping Adults | 2 | 77.7 | 48.1 | 118 | — |
|  | 4 | 84.8 | 51.3 | 143 | — |
|  | 8 | 83.8 | 49.5 | 143 | — |
| Control (3.0% dead after 143 hour exposure) | | | | | |

Discussion of Results

The juveniles were less susceptible to treatment than the adults, but did exhibit more of a response to increased levels of BULAB® 6002 polymer. Over 85% of the juveniles were prevented from attaching to the surface of the experimental dishes.

The adults were killed in a relatively short time and did not exhibit a dose response. The similar times to death of the normal as compared to the gaping adults indicates that BULAB® 6002 polymer is not an irritant which causes the clam to tightly close its valves to avoid exposure.

The data clearly demonstrates that BULAB® 6002 polymer will kill the Asiatic clam Corbicula in a reasonable time in both the larval and adult stages.

EXAMPLE 2

Discussion

The efficacy of a second straight-chain ionene polymer was demonstrated in similar laboratory experiments. Poly[2-hydroxyethylene(dimethyliminio)-2-hydroxypropylene(dimethyliminio) methylene dichloride], prepared as described in U.S. Pat. No. 4,140,798, was tested as a 60% aqueous solution, hereinafter referred to as BULAB® 6024 polymer.

Materials and Methods

The same materials and methods as in Example 1 were used except that the juveniles were obtained from clams being held in an experimental tank in the water system of a power station. Also, no experiments were done with gaping adults.

Experimental Results

The following is a summary of the results obtained from tests of BULAB ® 6024 polymer with the Asiatic clam, C. fluminea.

| Group | Treatment level (ppm) | Mean Time to Death (hr) | LT50 | LT100 | Mean Percent Not Attached |
|---|---|---|---|---|---|
| Juve- | 2 | 215.8 | 161.8 | 352 | 93.0 |
| niles | 4 | 181.3 | 132.4 | 304 | 86.4 |
|  | 8 | 140.2 | 82.3 | 257 | 70.3 |
| Control (21.5% dead after 352 hour exposure) | | | | | |
| Normal | 2 | 114.3 | 97.4 | 167 | — |
| Adults | 4 | 122.8 | 101.8 | 192 | — |
|  | 8 | 129.3 | 113.9 | 192 | — |
| Control (1.3% dead after 192 hour exposure) | | | | | |

Discussion of Results

The juveniles were less susceptible to treatment than the adults, but did exhibit more of a response to increased levels of BULAB ® 6024 polymer. At 2 ppm, over 90% of the juveniles were prevented from attaching to the surface of the experimental dishes.

Adults were killed by the treatment with BULAB ® 6024 polymer, but did not exhibit a dose response. The data demonstrate that BULAB ® 6024 polymer will kill the Asiatic clam Corbicula in a reasonable time in both the larval and adult stages.

EXAMPLE 3

Discussion

A branched-chain ionene polymer was tested against adult C. fluminea. The polymer tested was prepared from N,N,N',N'-tetramethylethylenediamine and epichlorohydrin as described in U.S. Pat. No. 4,018,592. It was tested as a 25% aqueous solution in water, hereinafter referred to as BULAB ® 5001 polymer.

Materials and Methods

The experimental design was essentially the same as that described in Example 1, except that only adults were used and only in normal condition, i.e., not gaping.

Experimental Results

The following is a summary of the results obtained from tests of BULAB ® 5001 polymer against adult Asiatic clams, C. fluminea.

| Group | Treatment level (ppm) | Mean Time to Death (hr) | LT50 | LT100 | Mean Percent Not Attached |
|---|---|---|---|---|---|
| Normal | 2 | >383 | 1042.7 | >383 | — |
| Adults | 4 | >383 | 305.1 | >383 | — |
|  | 8 | 186.3 | 160.1 | 311 | — |
| Control (1.3% dead after 383 hour exposure) | | | | | |

Discussion of Results

The adult clams were killed by BULAB ® 5001 polymer at a level of 8 ppm with evidence of a dose response. This indicates that while BULAB ® 5001 polymer is not as good as the straight-chain ionene polymers tested in Examples 1 and 2, branched-chain ionene poly- mers will also control the Asiatic clam C. fluminea at a relatively low treatment level.

While this invention has been described with respect to particular embodiments thereof, other forms or modifications of this invention will be evident to those skilled in the art. The appended claims, as well as the invention generally, should be construed to cover all such forms or modifications which are within the scope of the present invention.

We claim:

1. A method for the control of fouling by mollusks in an aqueous system comprising the step of adding to said aqueous system an amount of an ionene polymer effective for controlling fouling by mollusks.

2. The method of claim 1, wherein said mollusks are fresh water mollusks.

3. The method of claim 2, wherein said fresh water mollusks are Asiatic clams of the genus Corbicula.

4. The method of claim 3, wherein said aqueous system forms part of a nuclear or fossil-fueled power generating station.

5. The method of claim 1, wherein said mollusks are adults.

6. The method of claim 1, wherein said mollusks are juveniles.

7. The method of claim 1, wherein said aqueous system is the aqueous system of a cooling water system.

8. The method of claim 1, wherein said ionene polymer is a straight-chain ionene polymer.

9. The method of claim 1, wherein said ionene polymer is poly[oxyethylene(dimethyliminio)ethylene(dimethyliminio)ethylene dichloride].

10. The method of claim 1, wherein said ionene polymer is poly[2-hydroxyethylene(dimethyliminio)-2-hydroxypropylene (dimethyliminio)methylene dichloride].

11. The method of claim 1, wherein said ionene polymer is prepared from N,N,N',N'-tetramethylethylenediamine and epichlorohydrin.

12. A method for the control of fouling by mollusks in an aqueous system which comprises the step of adding to said aqueous system an ionene polymer in an amount effective for preventing the attachment of juvenile mollusks to a surface.

13. The method of claim 12, wherein said mollusks are Asiatic clams of the genus Corbicula.

14. The method of claim 12, wherein said aqueous system is the aqueous system of a cooling water system.

15. The method of claim 12, wherein said ionene polymer is a straight-chain ionene polymer.

16. The method of claim 12, wherein said ionene polymer is poly[oxyethylene(dimethyliminio)ethylene(dimethyliminio)ethylene dichloride].

17. The method of claim 12, wherein said ionene polymer is poly[2-hydroxyethylene(dimethyliminio)-2-hydroxypropylene (dimethyliminio)methylene dichloride].

18. The method of claim 12, wherein said ionene polymer is prepared from N,N,N',N'-tetramethylethylenediamine and epichlorohydrin.

19. A method for reducing the viability of a population of mollusks comprising the step of contacting at least a part of said population with an amount of an ionene polymer effective for reducing the viability of said population.

20. The method of claim 19, wherein said ionene polymer is poly[oxyethylene(dimethyliminio)ethylene(dimethyliminio)ethylene dichloride].

21. The method of claim 19, wherein said ionene polymer is poly[2-hydroxyethylene(dimethyliminio)-2-hydroxypropylene (dimethyliminio)methylene dichloride].

22. The method of claim 19, wherein said ionene polymer is prepared from N,N,N',N'-tetramethylethylenediamine and epichlorohydrin.

* * * * *